June 3, 1958 L. L. BROOKS Plant Pat. 1,714

AZALEA PLANT

Filed April 22, 1957

INVENTOR
LENARD L. BROOKS

United States Patent Office

Plant Pat. 1,714
Patented June 3, 1958

1,714

AZALEA PLANT

Lenard L. Brooks, Modesto, Calif.

Application April 22, 1957, Serial No. 654,433

1 Claim. (Cl. 47—60)

This invention is directed to a new and distinct variety of azalea plant, such plant being principally characterized by its large double indica type flowers in a beautiful and unusual shade of pink; its ease of reproduction on its own roots; its rapid yet many branched habit of growth; its large, glossy green leaves; and its high value as a greenhouse forcing or garden variety.

The instant variety is a sport of my variety Ecstasy, Plant Patent No. 1,157, discovered in the experimental section of my nursery at Modesto, California.

The sport as discovered by me was recognized as having great commercial value, cuttings were therefore taken for propagation and the plants thus produced carried forward all the distinguishing characteristics of the original sport. Three experimental propagations were made at Modesto, California, the plants resulting from each experimental propagation being allowed to develop and flower before cuttings were taken for the next experiment. In the three generations thus produced not one flower reverted to the original Ecstasy.

Referring now more specifically to the botanical details of the new and distinct variety of azalea plant, the following is an outline description of the same:

Plant:

*Form.*—Well branched, symmetrical form. The height and breadth of the young plants are usually about the same, but as the plants age, the breadth gradually becomes greater.

*Growing habit.*—Dense and bushy with an abundance of large, medium green leaves with good texture and weight. It grows very rapidly, often attaining a spread of three feet in four years from the rooted cutting. A minimum of pinching is required to produce well shaped plants.

*Blooming habit.*—Very profuse, flowering evenly over the entire plant at the same time when forced in the greenhouse or flowered naturally in the garden. It flowers profusely as a one-year plant.

*Blooming season.*—Plants growing in my garden bloom naturally in March to April. It forces easily out of season in the greenhouse. Pinched at the right time and grown properly it forces easily for Christmas.

Foliage:

*Size.*—Maximum size of mature leaves on thrifty young plants about 1⅜ inches wide and 2½ inches long, each plant having many smaller leaves. As the plants age the average size becomes smaller.

*Color.*—Growing under average conditions the color of the mature leaves are a yellow-green, plate 23–L–7, lighter beneath. With an ideal pH value and plenty of nitrogen in the soil the color becomes much deeper, plate 24–L–10.

*Shape.*—Ovate, pointed.

*Aspect.*—Glossy and smooth.

*Texture.*—Medium.

*Edge.*—Without serrations, some minute hairs.

*Ribs and veins.*—Normal.

Flower:

*Size.*—Three to 4 inches.

*Borne.*—One to 3 on each stem.

*Stem.*—Strong.

Figure 1:
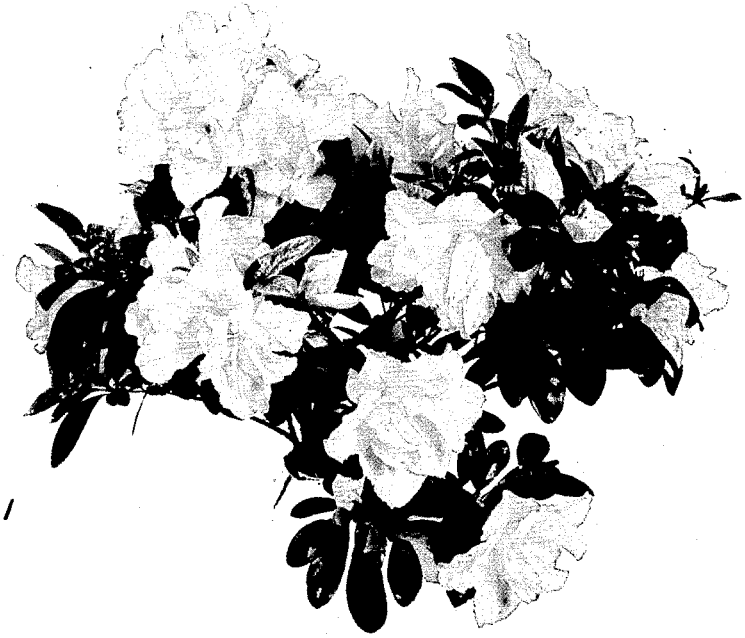
Fig. 1 is a perspective view of a plant in full bud and flower, showing many of the variations in the center construction of the flower.
Figure 2:
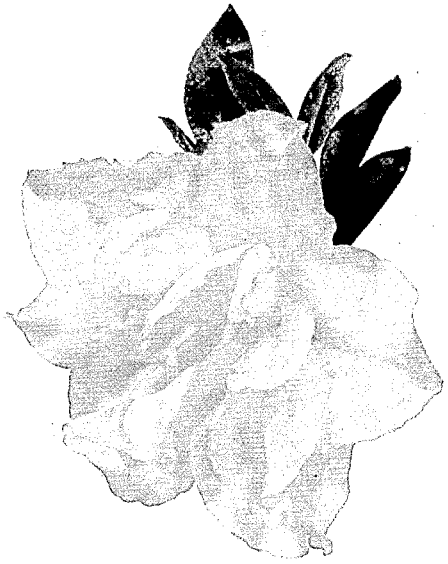
Fig. 2 is a stem with a flower in nearly natural size and showing nearly the maximum development of the petaloids in the center.

*Form.*—Commonly known as double (large Belgian indica type). The flower consists of a single hose or trumpet as found in the single azalea flower, except that the flower opens wider, and the petals are more reflexed, with a varying number of smaller petals or petaloids in the center. These petaloids are often antheriferous, usually standing quite erect rather than lying close to the outer trumpet as in the hose-in-hose azalea flower. The flower has a depth according to the length of the petaloids, which are often substantially the length of the outer petals. Figures 1 and 2 show the flowers in many of the various center formations.

*Permanence.*—Long lasting, retaining its beauty until the flowers are ready to fall.

*Petalage.*—Five reflexed petals on the outer flower, the center being composed of a varying number of petaloids; the latter being rarely more than seven in number and these are often antheriferous. Both the outer flower and petaloids are slightly ruffled. Rarely do the latter develop anthers when the maximum size is reached. The development of anthers has a direct effect on the size and shape of the petaloids; the anthers having a dwarfing and distorting effect, thus causing considerable variation in the center structure of the flower. The flower at lower right in Fig. 1 shows nearly the maximum development and the flower at upper right shows approximately the minimum development attained by the center structure of the flowers of this variety.

*Color.*—The color is pink, plate 41–J–3, varying some under different growing conditions. This is approximately the same shade of pink as that found in the variations in the petals of the variety Ecstasy (Plant Patent No. 1,157), of which this variety is a sport. The markings found in the upper part of the throat are yellow-green, similar to the throat markings found in the flowers of the variety Ecstasy. There is some lightening of the colors as the flowers age.

Petals.

*Texture.*—Substantial.

*Appearance.*—Velvety, inside and out, reflexed.

*Size.*—Average 1¼ to 1¾ inches wide and 1½ to 2¼ inches long.

*Shape.*—Ovate, narrowing abruptly at lower end.

*Arrangement.*—Normal indica type.

*Persistence.*—Remains firm until flower is ready to fall.

Reproductive organs.

*Stamens.*—Stamens do not usually occur in this variety, but if the maximum number of petaloids do not develop, some stamens may appear, usually only one or two. Anthers often develop on the petaloids and when this occurs, the petaloids become dwarfed and distorted, thus causing a wide variation in the center structure of the flowers. Anther is usually light reddish brown, darker with age. Filament, when it occurs is about the same color as the petals.

*Pollen.*—White.

*Style.*—The color of the style is similar to that of the petals. The length varies, but is often nearly two inches. The color of the stigma is similar to the throat markings. Both style and stigma are usually well developed.

*Ovaries.*—Normal.

All color plate identifications refer to "A Dictionary of Color" by Maerz and Paul.

*Comparison.*—This azalea is just like my variety Ecstasy (Plant Patent No. 1,157, of which this variety is a sport) in every way, except that the flowers are a beautiful shade of pink.

Like Ecstasy it starts very easily from cuttings and develops quickly into a fine symmetrical plant with a minimum of pinching, and it is an excellent garden or greenhouse forcing variety, flowering evenly over the entire plant whether flowered in the garden or forced in the greenhouse. It is an excellent mid-season forcer.

Having thus described the invention, I claim:

A new and distinct variety of azalea plant substantially as herein shown and described, characterized particularly by its large Belgian indica type double flowers in a distinctive shade of pink; the ease with which the cuttings root; and its rapid, many branched habit of growth when properly pinched.

No references cited.